United States Patent [19]
Butelman

[11] Patent Number: 4,990,522
[45] Date of Patent: Feb. 5, 1991

[54] ESTERIFIED EPHEDRINE DERIVATIVES WITH PROLONGED ANTIULCER ACTIVITY

[75] Inventor: Federico Butelman, Milan, Italy

[73] Assignee: Establissement Texcontor, Italy

[21] Appl. No.: 487,277

[22] Filed: Mar. 2, 1990

Related U.S. Application Data

[62] Division of Ser. No. 254,220, Oct. 6, 1988, Pat. No. 4,935,444.

[30] Foreign Application Priority Data

Oct. 23, 1987 [IT] Italy .................. 22407 A/87

[51] Int. Cl.$^5$ .................. C07D 213/55; C07D 333/38; C07D 233/66; A61K 31/44
[52] U.S. Cl. .................. 514/356; 546/285; 548/342; 549/71; 514/400; 514/448
[58] Field of Search .................. 548/342; 549/71; 546/285; 514/448, 399, 400, 356

[56] References Cited

U.S. PATENT DOCUMENTS 3,795,709  3/1974  Frey et al. .................. 260/618
3,911,017  10/1975  Hardtmann .................. 260/570.9

*Primary Examiner*—Alan L. Rotman
*Assistant Examiner*—Joseph K. McKane
*Attorney, Agent, or Firm*—Parkhurst, Wendel & Rossi

[57] ABSTRACT

Esterified ephedrine derivatives with prolonged antiulcer activity and low toxicity, having the following general formula:

(I)

in which R is:

$C_9H_{19}$      $C_{15}H_{31}$ $CH(NH_2)-CH_2-CH_2-COOH$      $CH(NH_2)-CH_2-\text{(imidazole)}$ $CH_2-CH_2-\text{(phenyl)}$      $C(CH_3)_3$ (thiophene)      pamoic acid radical;

(pyridine)      $-\text{(phenyl)}-OH$

The invention also describes a process for preparing derivatives of formula (I) and compositions containing them as active principle.

2 Claims, No Drawings

ESTERIFIED EPHEDRINE DERIVATIVES WITH PROLONGED ANTIULCER ACTIVITY

This application is a Rule 60 Divisional Application of Ser. No. 07/254,220, filed Oct. 6, 1988, now U.S. Pat. No. 4,935,444.

1. Field of the invention

This invention relates to esterified ephedrine derivatives with prolonged antiulcer activity and low toxicity.

2. Description of the prior art

Non-esterified ephedrine derivatives are known possessing antiulcer activity.

In particular, the compound WAS 4304 of European patent application No. 84108424.7 demonstrates very interesting antiulcer activity when administered intraperitoneally in experimental tests; however its $LD_{50}$ for this administration method is very low (115 mg/kg) and in addition its activity is of very limited duration.

SUMMARY OF THE INVENTION

We have now discovered esterified ephedrine derivatives which besides possessing high antiulcer activity have a lower toxicity and a more prolonged action than the compound WAS 4304 of the prior art.

The derivatives according to the present invention have the following general formula:

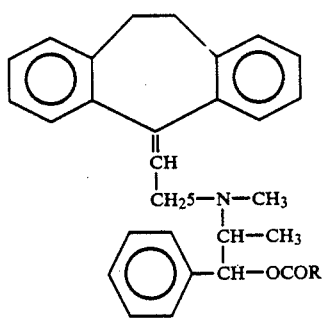

(I)

in which R is:

$C_9H_{19}$     $C_{15}H_{31}$ $CH(NH_2)-CH_2-CH_2-COOH$     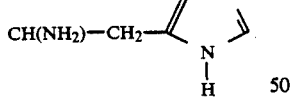

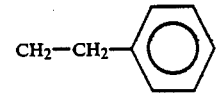     $C(CH_3)_3$

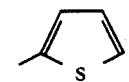     pamoic acid radical;

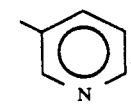     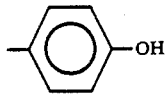

The invention also relates to a process for preparing the derivatives of general formula (I) and to the pharmaceutical compositions of antiulcer activity which contain at least one derivative of general formula (I) as active principle and a therapeutically acceptable carrier.

DETAILED DESCRIPTION OF THE INVENTION

The process for preparing the derivatives (I) of the present invention is implemented by the following stages:

(a) reacting the acid RCOOH, in which R has the aforesaid meaning, with thionyl chloride to obtain the corresponding acyl chloride;

(b) esterifying ephedrine (II) with RCOCl, in which R has the aforesaid meaning, to obtain the ester (III):

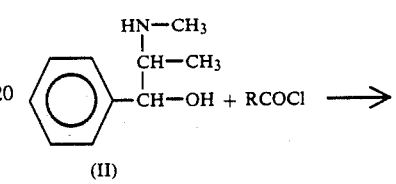

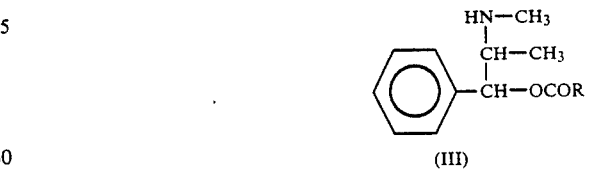

(c) condensing the tricyclic derivative (IV), in which X is a halogen, with the ester (III):

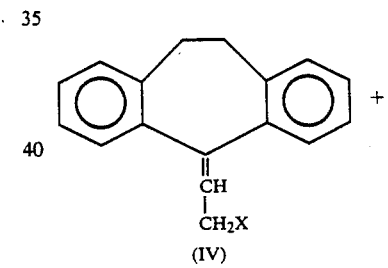

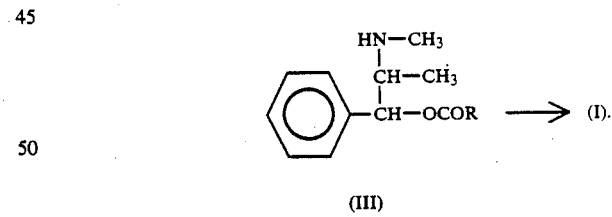

In those cases in which in addition to the carboxyl group other functional groups such as OH or $NH_2$ are bonded to the radical R, these functional groups are preferably firstly protected, and the condensation reaction is conducted preferably with the acid protected in this manner without passing through the acyl chloride.

Reaction (a) is conducted by treating the acid RCOOH with thionyl chloride at a temperature of between 30° and 50° C.

Reaction (b) is conducted by slowly adding the acyl chloride to the ephedrine at a temperature maintained between 2° C. and 8° C. and in the presence of an acid acceptor such as triethylamine or pyridine, this temperature then being maintained for 5-20 hours.

Alternatively, in the case of more reactive acyl chlorides, the procedure can be conducted in a solvent such as acetone or methylethylketone in the presence of sodium carbonate at a temperature of between 40° C. and the boiling point.

Reaction (c) is conducted in a reaction medium consisting of an organic solvent boiling under reflux in the present of an acid acceptor, and preferably in the presence of sodium bicarbonate.

Acetonitrile is preferably used as the organic solvent.

In the tricyclic derivative (IV), X is preferably Cl.

If the RCOOH acids contain functional hydroxyl groups, these groups are protected by esterification, preferably by the formation of the acetate, which is then reacted with the ephedrine (III), preferably by the dehydration method using dicyclohexylcarbodiimide (DCC) which in contrast to the acyl chloride method enables the hydroxyl protection group to be kept integral. This group is hydrolysed under mild conditions after reaction (c).

If the RCOOH acids contain functional amino groups, these are protected by t-butyloxycarbonyl (BOC) groups.

In these cases the reaction with ephedrine (III) is again preferably conducted by the dehydration method using dicyclohexylcarbodiimide (DOC) and the protection group is hydrolysed after reaction (c).

PHARMACOLOGICAL TRIALS

Those derivatives of the invention coded ET 2001, ET 2002, ET 2003 and ET 2004, as prepared in accordance with Examples 1, 2, 3 and 4 respectively, were tested in pharmacological trials to determine their acute toxicity and their antiulcer activity on ulcers induced by ligature of the pylorus and on ulcers induced by cold stress.

For comparison purposes the same trials were carried out using the product WAS 4304 described in European patent application No. 84108424.7.

1. ACUTE TOXICITY

Acute toxicity was determined on Swiss albino mice having an average weight of about 20 grams and on Wistar rats having an average weight of $150 \pm 10$ grams by endoperitoneal administration. All animals were kept fasting for 12 hours before the trial. For the trial, 10 animals, namely 5 males and 5 females, were used for each dose level.

The $LD_{50}$ values, expressed as mg/kg, are calculated on the basis of the mortality determined within eight days from administration, in accordance with the Lichtfield and Wilcoxon method. The results are given in the following Table 1.

TABLE 1

| $LD_{50}$ in the mouse and rat | | $LD_{50}$ mg/kg | | | | |
|---|---|---|---|---|---|---|
| Type of animal | Method of administration | WAS 4304 | ET 2001 | ET 2002 | ET 2003 | ET 2004 |
| Mouse | endoperitoneal | 127 | 585 | 535 | 580 | 630 |
| Rat | endoperitoneal | 87 | 510 | 590 | 618 | 681 |

2. ANTIULCER ACTIVITY against ulcers induced by ligature of the pylorus (Shay test): 
Groups of 10 Sprague Dawley rats of body weight between 200 and 250 grams were placed in cages under conditions of standard temperature ($21° \pm 2°$ C.), standard relative humidity (60–70%) and standard light (12 hours per day).

The animals were fed with rat pellets and with water at will.

The derivatives to be tested were administered orally 6, 12, 24 and 36 hours before ligature of the pylorus, after dispersion in physiological solution using Tween 80 as dispersant in a quantity of 1% and carboxymethylcellulose in a quantity of 0.2%. The volume administered was 10 ml/kg.

Before ligature, the rats had been kept without food for 18 hours but with free access to water, the pylorus ligature then being made under ether anesthetic, with suture of the peritoneum and of the abdominal wall.

The animals were then kept without food or water, and 18 hours after ligature were sacrificed using chloroform, their stomachs then being withdrawn and opened along the small curvature.

The gastric surface was extended to observe the ulcers, the evaluation being made by measuring their maximum width.

Table 2 shows the results obtained by administering the various derivatives at various times before ligature of the pylorus.

TABLE 2

| Antiulcer activity against ulcers induced by ligature of the pylorus | | | | |
|---|---|---|---|---|
| Active principle | $ED_{50}$ mg/kg by oral administration at various times before pylorus ligature | | | |
| | 6 h | 12 h | 24 h | 36 h |
| WAS 4304 | 0.2 | 1.1 | 1.8 | 2.4 |
| ET 2001 | 0.5 | 0.5* | 0.7* | 1.3* |
| ET 2002 | 0.4 | 0.5* | 0.8* | 1.1* |
| ET 2003 | 0.4 | 0.4* | 0.7* | 1.2* |
| ET 2004 | 0.5 | 0.4* | 0.6* | 1* |

*$P < 0.05$ $ED_{50}$ values of ET 2001, ET 2002, ET 2003, ET 2004 versus WAS 4304 at the same times of administration.

3. ANTIULCER ACTIVITY against ulcers induced by cold stress: 
This trial was carried out on Wistar rats weighing about 300 grams each.

The animals were divided randomly into groups of 10 animals each and kept without food for 18 hours before the trial, but had unrestricted water.

The active principles were administered to the animals orally in the form of a physiological solution which also contained 1% of Tween 80 and 0.2% of carboxymethylcellulose, one hour before securing to a laboratory board.

After ligature, the animals were placed in a refrigerator at a temperature of between 2° C. and 4° C. for two hours.

After this time the rats were sacrificed, their stomachs were withdrawn and opened along the small curvature, and the gastric mucosa checked.

The number of ulcers was counted and their relative diameters measured. From these individual data the mean value for each treatment group was obtained and the inhibition capacity calculated as a percentage relative to the control group, using the following formula:

$$\% = \frac{(T - C)}{C} \times 100$$

where C is the mean value in mm for the control group and T the mean value for the group treated with the derivative under examination.

Table 3 shows the results obtained by administering the derivatives under examination at different times before subjection to cold stress.

TABLE 3

| Active principle | Antiulcer activitiy against ulcers induced by cold stress $ED_{50}$ mg/kg by oral administration at various times before commencement of cold stress | | | |
|---|---|---|---|---|
| | 6 h | 12 h | 24 h | 36 h |
| WAS 4304 | 0.4 | 1.6 | 2.5 | 2.8 |
| ET 2001 | 0.4 | 0.9* | 1.2* | 2.1* |
| ET 2002 | 0.7 | 1* | 1.4* | 1.9* |
| ET 2003 | 0.6 | 0.9* | 1.3* | 1.7* |
| ET 2004 | 0.6 | 0.8* | 1.4* | 1.8* |

*$P < 0.05$ $ED_{50}$ values of ET 2001, ET 2002, ET 2003, ET 2004 versus WAS 4303 at the same times of administration.

DISCUSSION OF RESULTS

From Table 1 it can be seen that the $LD_{50}$ of the derivatives according to the invention is decidedly higher than that of WAS 4304.

From Tables 2 and 3 it can be seen that the $ED_{50}$ of the derivatives according to the invention is similar to that of WAS 4304 for administration 6 hours before commencement of the trial, whereas it is decidedly lower for administration 12, 24 and 36 hours before commencement of the trial.

Thus the derivatives according to the invention have lower toxicity and much more prolonged antiulcer activity than WAS 4304.

The long duration of action is very important in the treatment of gastric and/or duodenal ulcer because it enables gastric secretion to be carried to its physiological limits without incurring periods of achlorhydria because of hyperdosage, or secretion rebound because of underdosage.

It also simplifies chronic ingestion of the medicament; in this respect the administration of a medicament at a dosage rate of once or twice every two days is particularly well accepted by the patient and also enables a more personalized and precise treatment plan to be established for each patient.

The following examples of the preparation of the four derivatives used in the pharmacological trials are described for illustrative purposes only and have no limiting effect.

EXAMPLE 1

Preparation of (I) where $R = C_9H_{19}$ (derivative ET 2001)

The chloride of decanoic acid is prepared by reacting the acid (17.2 g, 0.1 mole) in thionyl chloride (23.8 g, 0.2 moles), heating the reaction mixture to 40° C. for 4 hours. The excess thionyl chloride is distilled off, followed by the acid chloride, which is reacted directly with ephedrine in the following manner: basic ephedrine (16.5 g, 0.1 mole) and pyridine (50 ml) are placed in a flask cooled with external ice, and the decanoic acid chloride (20 g, 0.106 moles) is added very slowly. The mixture is left at 5° C. for 12 hours, after which iced water is added slowly to precipitate the chloride of the ephedrine ester (23 g, 65%), which can be recrystallised from isopropyl ether, M.P. 100°–104° C.

| Elementary analysis for $C_{20}H_{34}NO_2Cl$ | | | |
|---|---|---|---|
| calculated | C 67.5% | H 9.6% | N 3.9% |
| found | C 67.75% | H 9.8% | N 4.1% |

This ester is reacted with an equimolar quantity of the tricyclic compound (IV) in 400 ml of acetonitrile in the presence of 10 g of $NaHCO_3$ under boiling reflux conditions for 6 hours.

The product obtained is filtered and crystallised from acetonitrile with a yield of 54%.

EXAMPLE 2

Preparation of (I) where

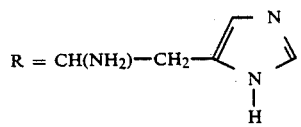

(derivative ET 2002)

Basic ephedrine (16.5 g, 0.1 mole) and DCC (20.6 g, 0.1 mole) are added at ambient temperature (18° C.) to a solution of t-butyloxy-carbonyl-histidine (25.5 g, 0.1 mole) in a mixture of ethyl acetate-dioxane (3:1, 100 ml). A mixture of ethyl acetate:hexane (2:1) is added and the dicyclohexylurea which forms is filtered off.

The formed ester is crystallised twice from methylene chloride-methanol, M.P. 148°–150° C.

| Elementary analysis for $C_{21}H_{30}N_4O_4C$ | | | |
|---|---|---|---|
| calculated | C 62.7% | H 7.5% | N 13.9% |
| found: | C 62.9% | H 7.7% | N 14.0% |

The ester prepared in this manner is reacted with the tricyclic compound (IV) under conditions analogous to Example 1, and only after this reaction the t-butyloxycarbonyl group is hydrolysed with trifluoroacetic acid at ambient temperature.

EXAMPLE 3

Preparation of (I) where

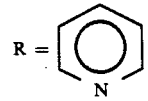

(derivative ET 2003)

Nicotinic acid chloride hydrochloride is prepared by reacting the acid (12 g, 0.1 mole) in thionyl chloride (23.8 g, 0.2 moles) by heating to 40° C. for 8 hours. The acid chloride hydrochloride is filtered off and is reacted directly with ephedrine in the following manner: basic ephedrine (16.5 g, 0.1 mole) and pyridine (50 ml) are placed in a flask cooled with external ice, and the nicotinic acid chloride hydrochloride (18.8 g, 0.106 moles) is added very slowly. The mixture is left for 12 hours at 5° C., after which iced water is slowly added to precipitate the ephedrine ester hydrochloride (20 g, 65%), which can be recrystallised from methanol/isopropyl ether. M.P. 172°–174° C.

| Elementary analysis for $C_{16}H_{19}N_2O_2$ | | | |
|---|---|---|---|
| calculated | C 62.2% | H 6.2% | N 9.1% |
| found | C 62.85% | H 6.4% | N 9.3% |

This ester can be reacted with the tricyclic compound (IV) under conditions analogous to Example 1, with a yield of 58%.

EXAMPLE 4

Preparation of (I) where

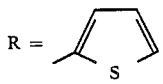

(derivative ET 2004)

The preparation is analogous to the preparation of Example 3.

I claim:

1. Esterified ephedrine derivatives of general formula:

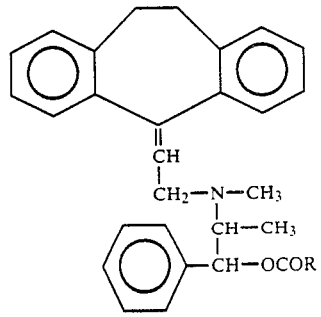

(I)

wherein R is selected from the group consisting of:

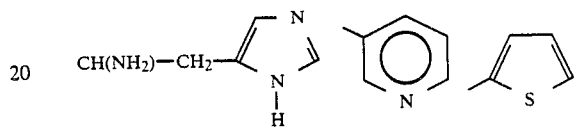

2. Pharmaceutical compositions comprising an anti-ulcer effective amount of a compound of claim 1 and a therapeutically acceptable carrier.

* * * * *